United States Patent [19]

Kobayashi et al.

[11] Patent Number: 4,476,328

[45] Date of Patent: * Oct. 9, 1984

[54] PROCESS FOR PRODUCING 3,3,3-TRIFLUOROPROPYL SUBSTITUTED PHENOL

[75] Inventors: Yoshiro Kobayashi, Tokyo; Itsumaro Kumadaki, Hachiohji; Masaaki Takahashi, Tokyo; Takashi Yamauchi, Iwaki, all of Japan

[73] Assignee: Kureha Kagaku Kogyo Kabushiki Kaisha, Tokyo, Japan

[ * ] Notice: The portion of the term of this patent subsequent to Apr. 13, 1999 has been disclaimed.

[21] Appl. No.: 320,538

[22] Filed: Nov. 12, 1981

Related U.S. Application Data

[62] Division of Ser. No. 233,714, Feb. 12, 1981, abandoned.

[30] Foreign Application Priority Data

Feb. 22, 1980 [JP] Japan .................... 55-21094
Nov. 21, 1980 [JP] Japan .................... 55-164435
Dec. 29, 1980 [JP] Japan .................... 55-186563
Dec. 29, 1980 [JP] Japan .................... 55-186564

[51] Int. Cl.$^3$ .......................................... C07C 37/14

[52] U.S. Cl. .................................. 568/775; 570/127; 568/639

[58] Field of Search ................. 570/127; 568/775, 639

[56] References Cited

U.S. PATENT DOCUMENTS 4,324,929 4/1982 Kobayashi et al. ................ 570/127

Primary Examiner—Bernard Helfin
Attorney, Agent, or Firm—Wegner & Bretschneider

[57] ABSTRACT

A novel trifluoropropyl derivative of mono-substituted benzene represented by the general formula:

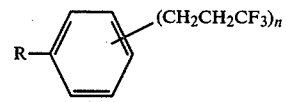

wherein R is halogen atom, hydroxy, trifluoromethyl, n-octyl, n-dodecyl, or phenoxy group not substituted or mono-substituted by 3,3,3-trifluoropropyl group, and n is an integer of 1, 2 or 3, with the proviso that the total number of 3,3,3-trifluoropropyl group of the derivative of mono-substituted benzene is at most 3, and a process for producing the derivative of mono-substituted benzene.

1 Claim, 10 Drawing Figures

PROCESS FOR PRODUCING 3,3,3-TRIFLUOROPROPYL SUBSTITUTED PHENOL

This application is a divisional of application Ser. No. 233,714 filed Feb. 12, 1981 and now abandoned.

BACKGROUND AND DETAILED DESCRIPTION OF THE INVENTION

The present invention relates to certain novel substituted benzene derivatives having at least one benzene ring substituted by at least one 3,3,3-trifluoropropyl group and to a novel process for producing the above-mentioned substituted benzene derivative.

The substituted benzene derivatives having benzene ring(s) substituted by 3,3,3-trifluoropropyl group(s) are useful for a variety of purposes. However, as an instance for synthesizing aromatic compounds having benzene ring(s) substituted by 3,3,3-trifluoropropyl group, only a process (U.S. Pat. No. 3,080,428) has been proposed in which 3,3,3-trifluoropropyl ether, $(CF_3CH_2CH_2)_2O$, is brought into reaction with benzene in the presence of hydrogen fluoride to form 3,3,3-trifluoropropylbenzene. Moreover, since in the above-mentioned process, water is formed in the reaction, the catalytic reactivity during the reaction is reduced and the recovery of the used catalyst is difficult. In addition, since the starting material of the reaction, 3,3,3-trifluoropropyl ether is synthesized by a low-yield (50 to 60%) reaction of hydrogen fluoride, formaldehyde or its polymer and very expensive vinylidene fluoride, the thus synthesized 3,3,3-trifluoropropyl ether is highly expensive.

It is an object of the present invention to produce a trifluoropropyl derivative of mono-substituted benzene represented by the formula:

wherein R is halogen atom, hydroxy, trifluoromethyl, n-octyl, n-dodecyl, or phenoxy group not substituted or mono-substituted by 3,3,3-trifluoropropyl group, and n is an integer of 1, 2 or 3, with the proviso that the total number of 3,3,3-trifluoropropyl group in said derivative of mono-substituted benzene is at most 3. A further object of the present invention is to provide a process for producing the above-mentioned derivative of mono-substituted benzene having at least one benzene ring substituted by at least one 3,3,3-trifluoropropyl group which comprises bringing a mono-substituted benzene of the formula, wherein $R^1$ is halogen atom, hydroxy, phenoxy, trifluoromethyl, n-octyl or n-dodecyl group, into reaction with 3,3,3-trifluoropropylene in the presence of an acid catalyst selected from the group consisting of hydrogen fluoride, boron trifluoride and a mixture thereof. Other object is to provide a 3,3,3-trifluoropropyl derivative of n-octyl- or n-dodecylbenzene obtained by bringing n-octylbenzene or n-dodecylbenzene into reaction with 3,3,3-trifluoropropylene in the presence of an acid catalyst selected from the group consisting of hydrogen fluoride, boron trifluoride and a mixture thereof.

In the drawing,

FIGS. 9 and 10 show those, respectively n-dodecyl-(3,3,3-trifluoropropyl)benzene.

The trifluoropropyl derivatives of mono-substituted benzene having at least one benzene ring substituted by at least one 3,3,3-trifluoropropyl group of the present invention are new chemical compounds useful for a variety of purposes. For example, n-octylbenzene derivatives and n-dodecylbenzene derivatives are used for a dielectric material.

In the cases where a mono-substituted benzene is brought into reaction with 3,3,3-trifluoropropylene, since the group $CF_3—$ is strongly electron-withdrawing, the basicity of the carbon-carbon double bond of 3,3,3-trifluoropropylene is far weaker than that of propylene, a presence of a strongly acidic Friedel-Crafts' catalyst is necessary in the reaction between the mono-substituted benzene and 3,3,3-trifluoropropylene. However, in this case, the use of aluminum chloride as a representative strongly acidic Friedel-Crafts' catalyst causes the substitution of halogen on the benzene ring and/or cyclization of the reactants.

Since the catalyst used in the present invention is a gaseous substance or a low-boiling liquid, the removal of the used catalyst is easily carried out by stripping, and the recovery and the reuse of the remaining catalyst are also easy. The catalyst is preferably used in the process of the present invention in an amount of more than 0.5 mole per mole of the mono-substituted benzene used as a starting material. In the case of n-octylbenzene or n-dodecylbenzene being used, the preferable catalyst is hydrogen fluoride or boron trifluoride. The temperature of the reaction of the process depends on the species of the starting materials and the catalyst, and from the viewpoint of the species and properties of the catalyst, the reaction temperature should be highest in the case of hydrogen fluoride, followed by boron trifluoride and then by a mixture thereof. On the other hand, from the viewpoint of the starting material, the temperature should be highest in the case of benzotrifluoride, followed by monohalogenobenzene and then by diphenyl ether and phenol.

Accordingly, for instance, the reaction is preferably carried out at $-20°$ to $150°$ C. in the presence of hydrogen fluoride, boron trifluoride or a mixture thereof, however, the actual temperature of the reaction is determined considering the reaction system, for instance, in the case of benzotrifluoride, the reaction is preferably carried out in the presence of the mixture of hydrogen fluoride and boron trifluoride at a temperature of 130° to 180° C.

Since in the process of the present invention, the mono-substituted benzene is brought into reaction with an industrial raw material, 3,3,3-trifluoropropylene in the presence of an acid catalyst to synthesize a trifluoropropyl derivative of mono-substituted benzene, not only the process necessitates only one reaction step, but also there is no formation of by-products such as water, and accordingly, the catalytic activity is maintained with the extremely easy recovery of the used catalyst.

Furthermore, while the derivative of mono-substituted benzene of the present invention is shown by the above-mentioned formula, the reaction product of a benzene or its derivative and propylene ($CH_3CH=CH_2$) is a benzene or its derivative substituted by isopropyl group, $(CH_3)_2CH-$. The difference of the two products is caused by the difference of basicity between the carbon-carbon double bond in 3,3,3-trifluoropropylene and that in propylene, the former being weaker than the latter, and this is the characteristic feature of the reaction adopted in the present invention.

That the derivative of mono-substituted benzene obtained by the process of the present invention has 3,3,3-trifluoropropyl group(s) has been confirmed by its $^1H$-NMR spectrum and $^{19}F$-NMR spectrum (Nuclear Magnetic Resonance spectrum).

After the above-mentioned reaction is over, the residual gas in the reaction system is purged, and then the residual catalyst is stripped followed by neutralization or washing with water and further distillation under a reduced pressure to obtain the product.

The trifluoropropyl derivative of mono-substituted benzene having at least one benzene ring substituted by at least one 3,3,3-trifluoropropyl group is useful, for instance, as a synthetic intermediate for producing pharmaceuticals and agricultural chemicals.

The followings are the more detailed explanation of the present invention while referring to non-limitative examples:

EXAMPLE 1

Into a stainless steel reaction tube, 94 g of phenol, 40 g of hydrogen fluoride and 96 g of trifluoropropylene were introduced, and boron trifluoride was pressured into the tube so that the internal pressure of the tube was made to 5 kg/cm²·G. The reaction was carried out at 40° C. for 24 hours while shaking the reaction tube vigorously. After the reaction was over, the gas in the tube was purged, and the content of the tube was poured into a mixture of iced water and sodium hydrogen carbonate. Then the mixture was extracted with dichloromethane and the extract was washed with water. After separating the organic layer from the aqueous layer, the former was dried and then subjected to evaporation for the removal of dichloromethane. The results of ion-gas chromatography with raising the temperature of the specimen of the residue of evaporation at a rate of 10° C. per min, of mass spectroscopy of the fractions of gas chromatography and of nuclear magnetic resonance spectrum of $^1H$ and $^{19}F$, respectively of gas chromatography were combined and shown in Table 1.

TABLE 1

| Component | Composition of the reaction product volatile in gas chromatography Composition (% by weight) based on the ratio of peak-areas of components appearing in the gas chromatogram of the residue of evaporation |
|---|---|
| Monosubstituted phenol by 3,3,3-trifluoropropyl group | 40.6 |
| Disubstituted phenol by 3,3,3-trifluoropropyl group | 14.6 |
| Trisubstituted phenol by 3,3,3-trifluoropropyl group | 7.3 |
| Unsubstituted phenol | 37.5 |

The identification of the above-mentioned components in Table 1 was based on the results of mass spectrography of the fractions of the residue of evaporation by gas chromatography and of nuclear magnetic resonance spectrum of $^1H$- and $^{19}F$-, respectively corresponding to those appearing as the peaks on gas chromatogram of the residue of evaporation.

By subjecting the thus obtained residue of evaporation to distillation under a reduced pressure of 4 mmHg, two fractions, namely, mono-(3,3,3-trifluoropropyl)-phenol boiling at 117° to 125° C./4 mmHg and bis(3,3,3-trifluoropropyl)phenol boiling at 165° to 192° C./4 mmHg were obtained.

The analytical data of mono-(3,3,3-trifluoropropyl)-phenol are as follows:

(a) Mass spectrography: $190(M^+)$ and $107(M^+-CH_2CF_3)$ (b) Nuclear magnetic resonance spectrography: No signal of methyl group was observed in $^1H$-NMR spectrum, and a signal of trifluoromethyl group was observed as a triplet in $^{19}F$-NMR spectrum in the position +2.8 ppm from the internal standard, benzotrifluoride.

(c) Elementary analysis:

|  | C (%) | H (%) | F (%) | O (%) |
|---|---|---|---|---|
| Found | 56.9 | 4.8 | 30.0 | 8.3 |
| Calcd. as $C_9H_9F_3O$ | 56.84 | 4.74 | 30.00 | 8.42 |

EXAMPLE 2

Into a stainless steel reaction tube, 6 g of chlorobenzene, 3 g of hydrogen fluoride and 3,3,3-trifluoropropylene were introduced, and boron trifluoride was pressured into the tube so that the internal pressure of the tube became 2 kg/cm²·G. The tube was heated to 135° C. to bring the content into reaction, the reaction having been carried out for 40 hours at the same temperature.

After the reaction was over, the gas in the tube was purged, and the content was treated as in Example 1. By subjecting the thus treated content to distillation under a reduced pressure, the three fractions were obtained, namely, 4.1 g of that of chloro-(3,3,3-trifluoropropyl)-benzene boiling at 76° C./25 mmHg, 1.2 g of that of chloro-bis(3,3,3-trifluoropropyl)benzene boiling at 105° to 108° C./8 mmHg and 0.2 g of that of chloro-tris(3,3,3-trifluoropropyl)benzene boiling at 176° to 198° C./5 mmHg.

The following are the analytical data of the three fractions:

(i) chloro-(3,3,3-trifluoropropyl)benzene:

(a) Mass spectrography: 208(M+), 173(M+—Cl) and 125(M+—CH$_2$CF$_3$)

(b) Nuclear magnetic resonance spectroscopy: No signal of methyl was found in $^1$H-NMR spectrum and a signal of trifluoromethyl was observed in $^{19}$F-NMR spectrum at the position of nearby +3.4 ppm from the internal standard, benzotrifluoride, as a triplet.

(c) Elementary analysis:

|  | C (%) | H (%) | Cl (%) | F (%) |
|---|---|---|---|---|
| Found | 52.0 | 3.8 | 17.1 | 27.1 |
| Calcd. as C$_9$H$_8$ClF$_3$ | 51.80 | 3.84 | 17.03 | 27.33 |

(ii) chloro-bis(3,3,3-trifluoropropyl)benzene:
 (a) Mass spectroscopy: 304(M+) and 221(M+—CH$_2$CF$_3$)

(iii) chloro-tris(3,3,3-trifluoropropyl)benzene:
 (a) Mass spectroscopy: 400(M+) and 317(M+—CH$_2$CF$_3$)

EXAMPLE 3

Into a 300-ml stainless steel autoclave, 100 g of bromobenzene and 66 g of 3,3,3-trifluoropropylene were introduced, and boron trifluoride was further pressured into the autoclave so that the internal pressure of the autoclave became 60 kg/cm$^2$·G. Then, the content was heated to 100° C. while stirring to bring it into reaction, and the reaction was carried out for 21 hours at 100° C. under agitation. After the reaction was over, the gas in the autoclave was purged and after dissolving the content of the autoclave into n-hexane, the hexane layer was washed with water and dried. After distilling n-hexane from the organic layer, the residue was examined by gas chromatography.

Table 3 shows the respective areas of peaks in the gas chromatogram, representing the compounds shown in Table 3, expressed by percentage of the total area of all the peaks.

TABLE 3

| Compounds | Area of each peak (%) (refer to Table 1) |
|---|---|
| Bromo-(3,3,3-trifluoropropyl)benzene | 42.2 |
| Bromo-bis(3,3,3-trifluoropropyl)benzene | 2.3 |
| Bromo-tris(3,3,3-trifluoropropyl)benzene | 0.1 |
| Bromobenzene | 55.4 |

The identification of the compounds in Table 3 was carried out as in Example 1.

By subjecting the above-mentioned residue to distillation under a reduced pressure, 48 g of bromo-3,3,3-trifluoropropylbenzene boiling at 90° to 93° C./4 mmHg was obtained. The followings are the analytical data of bromo-3,3,3-trifluoropropylbenzene:

(a) Mass spectroscopy: 252(M+) and 169 (M+—CH$_2$CF$_3$)

(b) Elementary analysis:

|  | C (%) | H (%) | Br (%) | F (%) |
|---|---|---|---|---|
| Found | 42.5 | 3.2 | 31.9 | 22.4 |
| Calcd. as C$_9$H$_8$BrF$_3$ | 42.69 | 3.16 | 31.62 | 22.53 |

(c) Nuclear magnetic resonance spectrometry
 $^1$H-NMR: δ1.9∼3.2 ppm (m, 4H: —CH$_2$—), δ6.9∼7.7 ppm (m, 4H: Ar—H).

$^{19}$F-NMR: a signal due to trifluoromethyl group was observed in the neighbourhood of position of +2.5 ppm from that of benzotrifluoride as an internal standard.

EXAMPLE 4

Into a stainless steel reaction tube, 13 g of benzotrifluoride, 5 g of hydrogen fluoride and 10 g of 3,3,3-trifluoropropylene were introduced, and boron trifluoride was pressured into the tube so that the internal pressure of the tube became to 2 kg/cm$^2$·G and by heating the tube at 165° C. and keeping at the same temperature for 24 hours, the reaction was carried out. After the reaction was over, the gas within the tube was purged, and the content of the tube was treated as in Example 1. The thus treated content was subjected to distillation under a reduced pressure to give the following three fractions, namely, 1.5 g of the first fraction of (3,3,3-trifluoropropyl)benzotrifluoride boiling at 65° to 68° C./18 mmHg, 5.9 g of the second fraction of bis(3,3,3-trifluoro)benzotrifluoride boiling at 88° to 91° C./7 mmHg and 2.6 g of the third fraction of tris(3,3,3-trifluoropropyl)benzotrifluoride boiling at 188° to 192° C./9 mmHg. The analytical data on the three fractions are shown as follows:

(i) (3,3,3-trifluoropropyl)benzotrifluoride:
 (a) Mass spectroscopy: 242(M+) and 159(M+—CH$_2$CF$_3$)

(b) Nuclear magnetic resonance spectrography: No signal of methyl group was observed on $^1$H-NMR spectrum and a signal of trifluoromethyl was observed as a triplet in $^{19}$F-NMR spectrum nearby +4.0 ppm from the benzotrifluoride as the internal standard.

(c) Elementary analysis:

|  | C (%) | H (%) | F (%) |
|---|---|---|---|
| Found | 49.8 | 3.1 | 47.1 |
| Calcd. as C$_{10}$H$_8$F$_6$ | 49.59 | 3.31 | 47.10 |

(ii) Bis(3,3,3-trifluoropropyl)benzotrifluoride
 (a) Mass spectrography: 338(M+) and 255 (M+—CH$_2$CF$_3$)

EXAMPLE 5

Into a one-liter stainless steel autoclave, 340 g of diphenyl ether and 230 g of 3,3,3-trifluoropropylene were introduced, and further boron trifluoride was pressured into the autoclave so that the internal pressure was raised from 2 to 58 kg/cm$^2$·G. Then the content of the autoclave was heated to 50° C. and kept at the same temperature for 20 hours to bring the content into reaction. After the reaction was over, the content was collected, washed with water and dried while following the conventional procedures. The gas chromatographical examination of the thus treated reaction mixture gave the results in the same manner as in Example 1, in Table 4.

TABLE 4

| Compound | Area of each peak (%) (refer to Table 1) |
|---|---|
| Monosubstituted diphenyl ether by 3,3,3-trifluoropropyl group | 53.1 |
| Disubstituted diphenyl ether by 3,3,3-trifluoropropyl group | 18.9 |
| Trisubstituted diphenyl ether by 3,3,3-trifluoropropyl group | 10.9 |
| Unsubstituted diphenyl ether | 17.1 |

Identification of the compounds in Table 4 was carried out as in Example 1.

By subjecting the above-mentioned reaction mixture to fine distillation under a reduced pressure, three fractions boiling respectively at 103° C./2 mmHg, 124° C./2 mmHg and 135° to 137° C./2 mmHg were obtained, the first fraction being mono-substituted diphenyl ether, the second fraction being disubstituted diphenyl ether and the third fraction being trisubstituted diphenyl ether, three fractions having respective purities higher than 99%. Their structures were confirmed by their mass spectra and their nuclear magnetic resonance spectra to be those shown above, respectively.

(a) Nuclear magnetic resonance spectrometry $^1$H-NMR: $\delta 1.9 \sim 3.0$ ppm (m, 4H: —CH$_2$—) $\delta 6.6 \sim 7.5$ ppm (m, 9H: Ar—H)

$^{19}$F-NMR: a signal due to trifluoromethyl group was observed in the neighbourhood of position of +3.9 ppm from that of benzotrifluoride as an internal standard.

EXAMPLE 6

Figure 6:
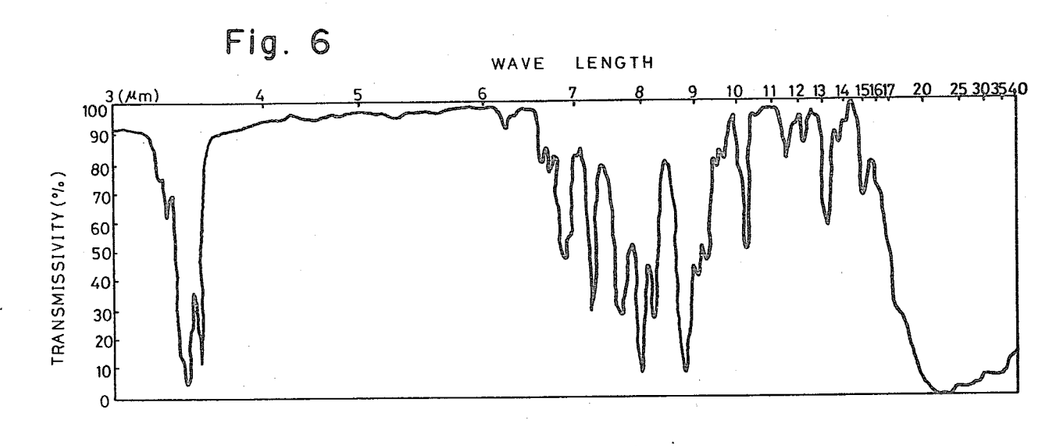

In a stainless steel autoclave of a capacity of one liter, 262 g of n-octylbenzene and 172 g of 3,3,3-trifluoropropylene were introduced in the above-mentioned order, and then boron trifluoride was pressured into the autoclave to the internal pressure of 70 kg/cm$^2$·G. After that, while maintaining the autoclave at a temperature of 40° C., the reaction was carried out for 17 hours with stirring. After the reaction was over, the gas in the autoclave was purged, and the content of the autoclave was poured into a mixture of iced water and sodium hydrogen carbonate. Then the mixture was extracted with dichloromethane and the extract was washed with water. After separating the organic layer from the aqueous layer, the former was dried and then subjected to evaporation for the removal of dichloromethane. By subjecting the resultant reaction mixture to a fine distillation under a reduced pressure, 182 g of a fraction boiling at 111° to 117° C./0.9 mmHg was obtained. That the fraction contained more than 99% of a novel compound, n-octyl-(3,3,3-trifluoropropyl)benzene, was confirmed by gas-chromatography and the following results of analyses:

(a) Mass spectrographical analysis at 20 eV: (m/e) 286 The mass spectrogram is shown in FIG. 6.

(b) Nuclear magnetic resonance spectrometry (CCl$_4$ soln)

$^1$H-NMR: $\delta 6.9 \sim 7.3$ ppm (m, 4H: Ar—H) $\delta 1.1 \sim 3.2$ ppm (m, 18H: —CH$_2$—) $\delta 0.9$ ppm (t, 3H:—CH$_3$)

$^{19}$F-NMR: a signal due to trifluoromethyl group was observed in the neighbourhood of positions from +2.8 and +3.0 ppm of that of benzotrifluoride as an internal standard as the overlap of two kinds of triplet.

(c) Elementary analysis:

|  | C (%) | H (%) | F (%) |
| --- | --- | --- | --- |
| Found | 71.5 | 8.7 | 19.8 |
| Calcd. as C$_{17}$H$_{25}$F$_3$ | 71.33 | 8.74 | 19.93 |

Figure 1:
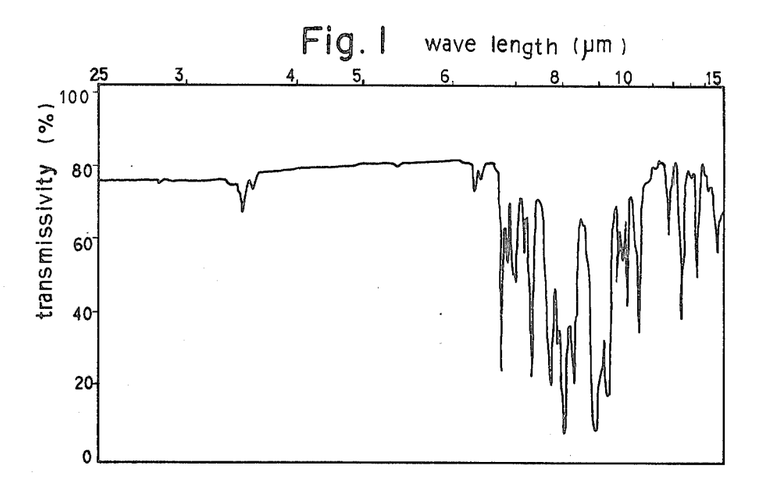
FIG. 1 shows the infrared absorption spectrum of (3,3,3-trifluoropropyl)phenol.
Figure 2:
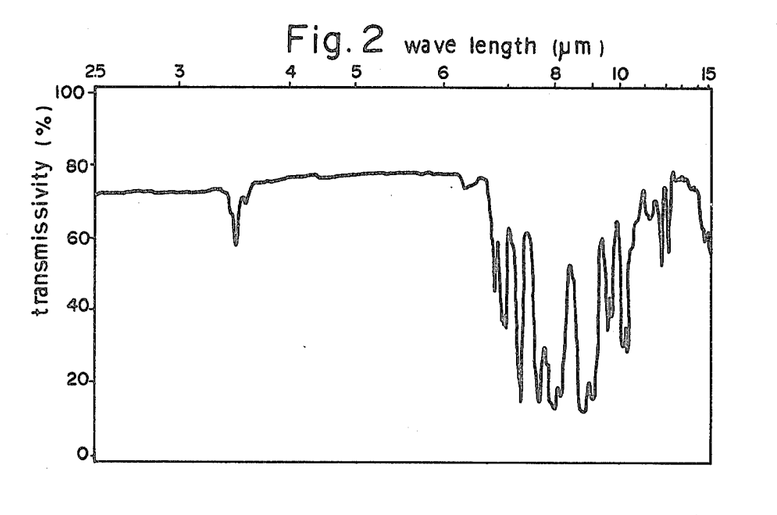
FIG. 2 shows that of chloro-(3,3,3-trifluoropropyl)-benzene.
Figure 3:
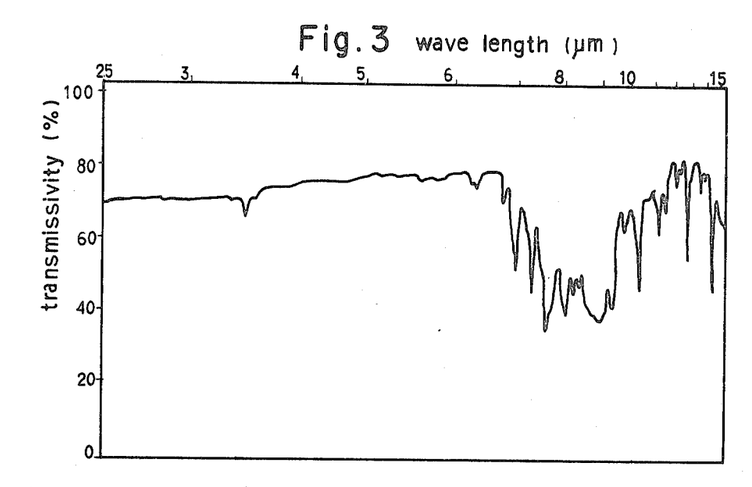
FIG. 3 shows that of chloro-bis(3,3,3-trifluoropropyl)benzene.
Figure 4:
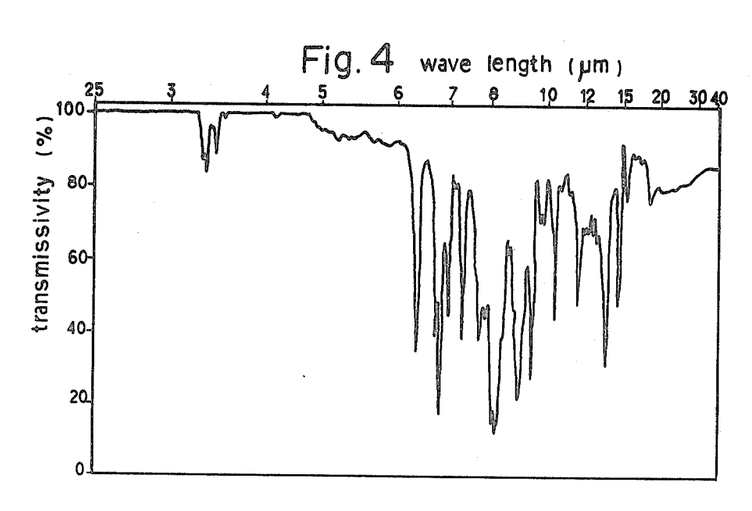
FIG. 4 shows that of (3,3,3-trifluoropropyl)benzotrifluoride.
Figure 5:
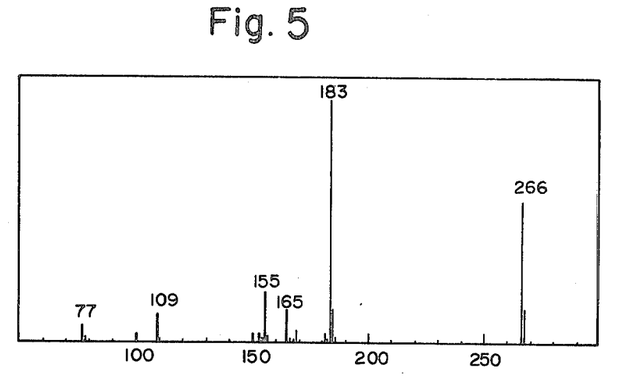
FIGS. 5 and 6 show the infrared absorption spectrum and the mass spectrum, respectively of phenyl (3,3,3-trifluoropropyl)phenyl ether.

(d) Infrared absorption spectrometry: The infrared absorption spectrogram was shown in FIG. 5.

(e) B.p.: 111°~117° C./0.9 mmHg (f) Specific gravity: 1.006 (20° C.)

(g) Refractive index: 1.4547 (20° C.)

The electrical properties of n-octyl(3,3,3-trifluoropropyl)benzene are shown in Table 5.

TABLE 5

| Dielectric constant | 4.18 |
| --- | --- |
| Dielectric loss (tan$\delta$) (%) | 0.095 |
| Volume resistivity ($\Omega$ · cm) | $1.08 \times 10^{14}$ |

EXAMPLE 7

Figure 8:
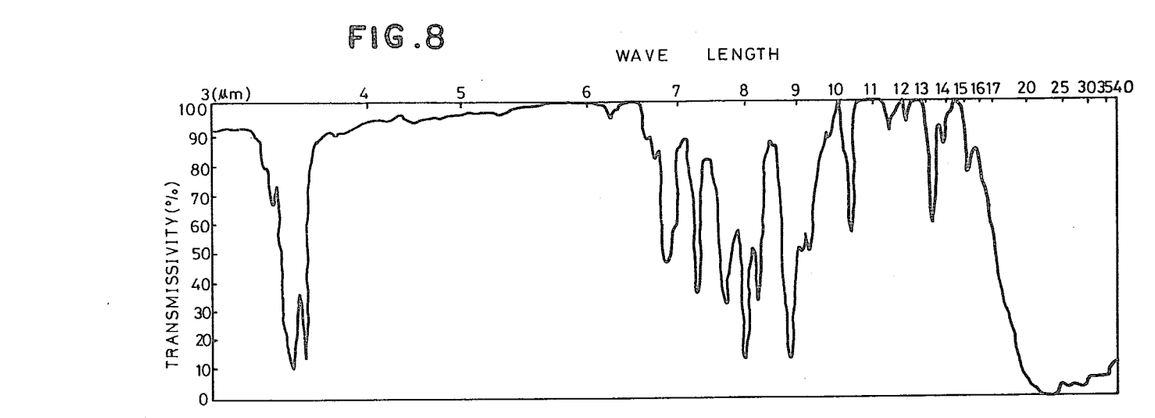
Figure 9:
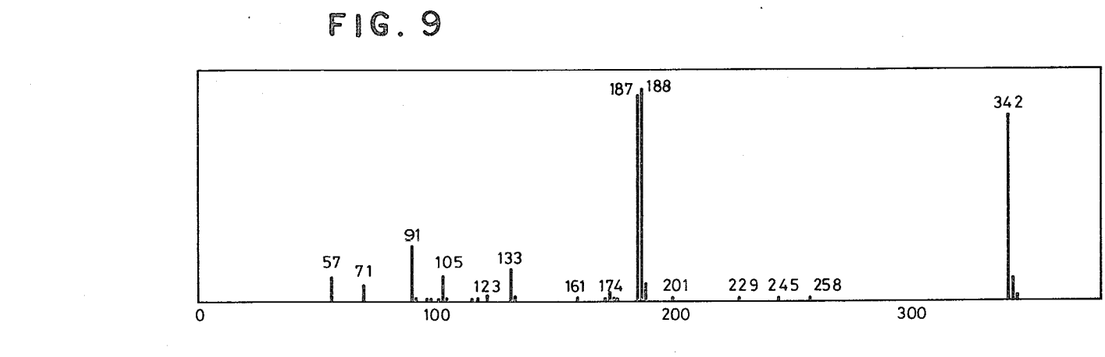

In a stainless steel autoclave of capacity of one liter, 369 g of n-dodecylbenzene and 166 g of 3,3,3-trifluoropropylene were introduced in the above-mentioned order, and then boron trifluoride was pressured into the autoclave to the internal pressure of 73 kg/cm$^2$·G. After that, while maintaining the autoclave at a temperature of 40° C., the reaction was carried out for 18 hours while stirring. After the reaction was over, the gas in the autoclave was purged, and the content of the autoclave was poured into a mixture of iced water and sodium hydrogen carbonate. Then the mixture was extracted with dichloromethane and the extract was washed with water. After separating the organic layer from the aqueous layer, the former was dried and then subjected to evaporation for the removal of dichloromethane. By subjecting the resultant reaction mixture to a fine distillation under a reduced pressure, 117 g of a fraction boiling at 154° C./0.8 mmHg to 152° C./0.65 mmHg was obtained. That the fraction contained more than 99% of a novel compound, n-dodecyl-(3,3,3-trifluoropropyl)benzene, was confirmed by gas-chromatography and the following results of analyses:

(a) Mass spectrographical analysis at 20 eV: (m/e) 342 The mass spectrogram is shown in FIG. 8.

(b) Nuclear magnetic resonance spectrometry (CCl$_4$ soln)

$^1$H-NMR: $\delta 7.0 \sim 7.3$ ppm (m, 4H: Ar—H) $\delta 1.1 \sim 3.2$ ppm (m, 26H: —CH$_2$—) $\delta 0.9$ ppm (t, 3H: —CH$_3$)

$^{19}$F-NMR: a signal due to trifluoromethyl group was observed in the neighbourhood of positions from +2.7 and +2.9 ppm of that of benzotrifluoride as an internal standard as the overlap of two kinds of triplet.

(c) Elementary analysis:

|  | C (%) | H (%) | F (%) |
| --- | --- | --- | --- |
| Found | 73.9 | 9.6 | 16.5 |
| Calcd. as C$_{22}$H$_{33}$F$_3$ | 73.68 | 9.65 | 16.67 |

Figure 7:
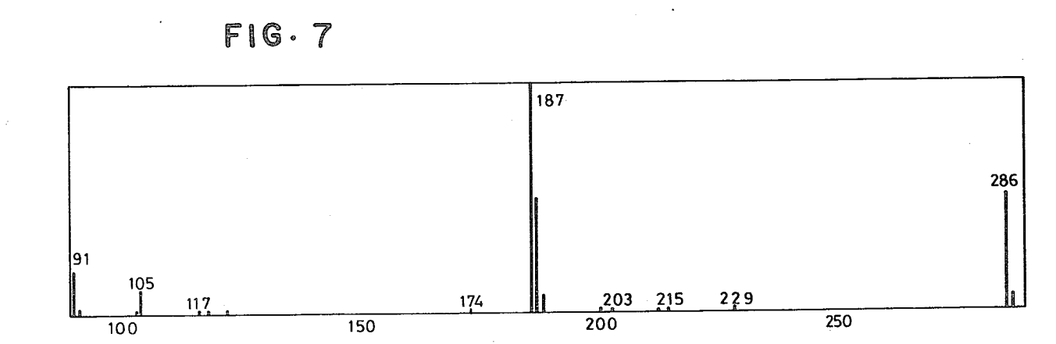
FIGS. 7 and 8 show those, respectively of n-octyl-(3,3,3-trifluoropropyl)benzene.

(d) Infrared absorption spectrometry: The infrared absorption spectrogram was shown in FIG. 7.

(e) B.P.: 154° C./0.8 mmHg to 152° C./0.65 mmHg (f) Specific gravity: 0.978 (20° C.)

(g) Refractive index: 1.4561 (20° C.)

The electrical properties of n-octyl-(3,3,3-trifluoropropyl)benzene at a temperature of 20° C. are shown in Table 6.

TABLE 6

| Dielectric constant | 3.89 |
| --- | --- |
| Dielectric loss (tan$\delta$) (%) | 0.015 |
| Volume resistivity ($\Omega$ · cm) | $8.79 \times 10^{14}$ |

What is claimed is:

1. A process for producing a substituted benzene derivative having at least one benzene ring substituted by at least one 3,3,3-trifluoropropyl group which comprises bringing monosubstituted benzene represented by the formula wherein $R^1$ is hydroxy group, into reaction with 3,3,3-trifluoropropylene in the presence of an acid catalyst selected from the group consisting of hydrogen fluoride, boron trifluoride and a mixture thereof.

* * * * *